(12) United States Patent
Schumacher (10) Patent No.: US 8,465,528 B2
(45) Date of Patent: Jun. 18, 2013

(54) SURGICAL RETAINING SCREW

(75) Inventor: Joerg Schumacher, Teltow (DE)

(73) Assignee: Aesculap AG, Tuttlingen (DE)

( * ) Notice: Subject to any disclaimer, the term of this patent is extended or adjusted under 35 U.S.C. 154(b) by 896 days.

(21) Appl. No.: 12/231,307

(22) Filed: Aug. 28, 2008

(65) Prior Publication Data

US 2009/0069853 A1 Mar. 12, 2009

(30) Foreign Application Priority Data

Aug. 30, 2007 (DE) .......................... 10 2007 042 959

(51) Int. Cl.
*A61B 17/70* (2006.01)
(52) U.S. Cl.
USPC .......................................... 606/273; 606/270
(58) Field of Classification Search
USPC ................. 606/301, 265–270, 271–273, 246
See application file for complete search history.

(56) References Cited

U.S. PATENT DOCUMENTS

| | | | |
|---|---|---|---|
| 2,384,953 A * | 9/1945 | Miller ........................... | 411/237 |
| 5,207,678 A | 5/1993 | Harms et al. | |
| 5,474,555 A | 12/1995 | Puno et al. | |
| 5,716,356 A | 2/1998 | Biedermann et al. | |
| 5,810,819 A * | 9/1998 | Errico et al. ................... | 606/266 |
| 6,077,262 A | 6/2000 | Schläpfer et al. | |
| 6,090,111 A | 7/2000 | Nichols | |
| 6,251,112 B1 * | 6/2001 | Jackson ......................... | 606/916 |
| 6,485,492 B1 | 11/2002 | Halm et al. | |
| 6,565,565 B1 * | 5/2003 | Yuan et al. ..................... | 606/272 |
| 7,211,086 B2 | 5/2007 | Biedermann et al. | |
| 7,223,268 B2 | 5/2007 | Biedermann | |
| 2003/0100904 A1 | 5/2003 | Biedermann | |
| 2003/0125741 A1 * | 7/2003 | Biedermann et al. ........... | 606/61 |
| 2003/0153911 A1 | 8/2003 | Shluzas | |
| 2003/0199873 A1 | 10/2003 | Richelsoph | |
| 2004/0097933 A1 | 5/2004 | Lourdel et al. | |
| 2004/0236330 A1 | 11/2004 | Purcell et al. | |
| 2005/0119667 A1 | 6/2005 | Leport et al. | |
| 2005/0131410 A1 * | 6/2005 | Lin ................................ | 606/61 |
| 2005/0203516 A1 * | 9/2005 | Biedermann et al. ........... | 606/61 |

(Continued)

FOREIGN PATENT DOCUMENTS

| | | |
|---|---|---|
| DE | 41 10 002 | 5/1992 |
| DE | 41 07 480 | 9/1992 |

(Continued)

*Primary Examiner* — Nicholas Woodall
*Assistant Examiner* — Larry E Waggle, Jr.
(74) *Attorney, Agent, or Firm* — Lipsitz & McAllister, LLC (57) ABSTRACT

In order to simplify the construction and handling capability of a surgical retaining screw comprising a shaft which has an external thread, a head part which is connected to the shaft securely or movably and has an interior space open towards the upper side located opposite the shaft as well as two openings which are arranged on oppositely located sides of the head part, are open towards the upper side and form a receptacle for a bar-like connecting part, and a clamping screw which can be screwed into the interior space from the upper side in such a manner that it clamps a connecting part placed in the receptacle in this receptacle, it is suggested that the clamping screw be screwed into a screw sleeve which abuts with a conical outer surface tapering towards the upper side of the head part on the complementary conical inner surface of a bearing sleeve surrounding the screw sleeve and that the bearing sleeve be held on the head part to as to be secured against any displacement in the direction towards the upper side.

25 Claims, 9 Drawing Sheets

U.S. PATENT DOCUMENTS

| | | |
|---|---|---|
| 2005/0267472 A1 | 12/2005 | Biedermann et al. |
| 2006/0009773 A1* | 1/2006 | Jackson .......................... 606/73 |
| 2006/0036252 A1* | 2/2006 | Baynham et al. ................ 606/73 |
| 2006/0095038 A1 | 5/2006 | Jackson |
| 2006/0167455 A1* | 7/2006 | Clement et al. ................. 606/61 |
| 2006/0293664 A1 | 12/2006 | Schumacher |
| 2007/0260246 A1 | 11/2007 | Biedermann |
| 2007/0286703 A1 | 12/2007 | Doubler et al. |
| 2008/0294202 A1 | 11/2008 | Peterson et al. |

FOREIGN PATENT DOCUMENTS

| | | |
|---|---|---|
| DE | 198 35 816 | 2/2000 |
| DE | 299 23 489 | 11/2000 |
| DE | 101 57 814 | 6/2003 |
| DE | 101 64 323 | 6/2003 |
| DE | 10 2005 021 879 | 11/2006 |
| WO | 2004/047657 | 6/2004 |
| WO | 2006/116606 | 11/2006 |

* cited by examiner

SURGICAL RETAINING SCREW

This application claims the benefit of German patent application no. 10 2007 042 959.4 filed Aug. 30, 2007, which is incorporated herein and made a part hereof by reference.

BACKGROUND OF THE INVENTION

The invention relates to a surgical retaining screw comprising a shaft with an external thread, a head part which is connected to the shaft securely or movably and has an interior space open towards the upper side located opposite the shaft as well as two openings which are arranged on oppositely located sides of the head part, are open towards the upper side and form a receptacle for a bar-like connecting part, and a clamping screw which can be screwed into the interior space from the upper side in such a manner that it securely clamps a connecting part placed in the receptacle in this receptacle.

Surgical retaining screws of this type can be used in various ways for stabilizing and securing bones and bone fragments in place; the surgical retaining screws can, for example, be pedicle screws. Surgical retaining screws of this type are, however, also used at other parts of the body for securing bones and bone fragments in place.

Clamping devices of very different types are known for securing a connecting part to the head part of a surgical retaining screw; for example, a clamping nut can be screwed onto a head part with an external thread (U.S. Pat. No. 5,474,555) or it is known to securely clamp the connecting parts by means of a clamping piece which can be screwed into the head part from the side (U.S. Pat. No. 6,090,111).

In other constructions, separate bearing elements, which surround the head part on the outside and into which a clamping screw is screwed, are placed on the head part (DE 41 10 002 C2; DE 41 07 480 C2; WO 2004/047657 A2; US 2005/0119667 A1).

In all these cases a relatively complicated construction results; in addition, measures must be taken to avoid any undesired spreading apart of the head part and, finally, undesired stress concentrations in the head part, as a result of which the strength can be impaired, occur in many constructions.

The object of the invention is to design a generic surgical retaining screw such that the assembly and the secure clamping of the connecting part are simplified; in addition, the strength characteristics of the arrangement are intended to be improved.

SUMMARY OF THE INVENTION

This object is accomplished in accordance with the invention, in a surgical retaining screw of the type described at the outset, in that the clamping screw is screwed into a screw sleeve which abuts with a conical outer surface, which tapers towards the upper side of the head part, on the complementary conical inner surface of a bearing sleeve surrounding the screw sleeve and that the bearing sleeve is held on the head part so as to be secured against any displacement in the direction towards the upper side.

Such an attachment works in accordance with the principle of an expanding cone; the screw sleeve is drawn into the bearing sleeve in an axial direction as a result of the screw-in forces of the clamping screw and a frictional connection results between screw sleeve and bearing sleeve as a result of the conical design of the outer surface of the screw sleeve and the inner surface of the bearing sleeve; the forces acting radially outwards are absorbed not only by the screw sleeve but also by the bearing sleeve and do not act on the head part which, as a result, does not experience any undesired spreading apart. In addition, insertion is simplified considerably because, first of all, no rotary movement, such as that required for screwing on nuts or screwing in screws, is necessary for the insertion; it is sufficient for the purpose of assembly to, first of all, draw the screw sleeve into the bearing sleeve in order to place the constructional unit consisting of screw sleeve, bearing sleeve and clamping screw, which is screwed into the screw sleeve, in position on the head part. A rotational movement, namely for screwing in the clamping screw, is not required until the final clamping of the connecting part.

It is favorable when the angle of inclination of the conical outer surface in relation to the central axis of the screw sleeve is between 0° and 30°. When the angles of inclination are relatively small, self-locking occurs when the two parts are clamped to one another.

In one preferred embodiment, it is provided for the bearing sleeve to be arranged in the interior space and, in order to secure it against any displacement in the direction towards the upper side of the head part, bearing sleeve and head part have projections and recesses which engage in one another. For example, the bearing sleeve can have, on its outer side, one or more projections which engage in recesses on the inner side of the head part.

In one preferred embodiment, it is provided for the projection on the bearing sleeve to be an annular shoulder which projects outwards.

The recess on the head part can accordingly be an arc-shaped groove on the inner side of the interior space.

It is favorable when the annular shoulder has an upper side ascending towards the outside, in particular, when the recess also has an upper side sloping down towards the interior space. As a result of these inclined contact surfaces it is ensured that the two sections of the head part which are formed by the openings forming the receptacle are drawn together due to the forces acting on the bearing sleeve; this, therefore, counteracts any undesired spreading apart.

In another embodiment, it may be provided for the recess to be formed by an opening in the wall of the head part; a projection on the bearing sleeve snaps into this opening.

In this respect, it is advantageous when the bearing sleeve and the head part are designed in such a manner that the bearing sleeve can be pushed into the interior space from the upper side of the head part until the projection or projections engage in the recesses of the head part. In this respect, the screw sleeve can, in particular, be already inserted loosely into the bearing sleeve; the clamping screw can be screwed into the screw sleeve such that this constructional unit consisting of bearing sleeve, screw sleeve and clamping screw can be inserted into the head part from above once the connecting part has been inserted from above.

The bearing sleeve can be compressible radially in the area of the projections or recesses. In addition or alternatively, it may be provided for the head part to be elastically expandable in the area of the projections or recesses. The engagement of the projections in the recesses is made possible by an elastic deformation of the bearing sleeve and/or of the head part; an elastic snap-in connection, therefore, results.

In this respect, it is favorable when the bearing sleeve is subdivided by longitudinal slits into sections which are located next to one another and can be bent elastically against one another.

Furthermore, it may be provided for the projections to have slide-on surfaces, by means of which the entry of the projections into the recesses is made possible during the insertion of the bearing sleeve into the interior space; the projections on the parts located respectively opposite one another slide on the slide-on surfaces and deform the head part and/or the bearing sleeve elastically.

In another embodiment, it is provided for the projections and recesses to be circumferential grooves on the outer side of the bearing sleeve and the inner side of the head part.

In one preferred embodiment of the invention, the bearing sleeve has a radially projecting flange which abuts on the upper side of the head part when the bearing sleeve is inserted and, therefore, limits the insertion depth of the bearing sleeve into the head part.

The radially projecting flange can, in addition, have at its outer edge an annular wall section which abuts on the outer wall of the head part when the bearing sleeve is inserted.

The clamping screw, in the screwed-in state, can abut directly on the connecting part and clamp it, as a result; in a modified embodiment it is provided for the clamping screw, in the screwed-in state, to abut on a clamping element which is pressed onto the connecting part by the clamping screw when screwed in.

In a particularly preferred embodiment, it is provided for the clamping screw to have an extension for accommodating a rotary tool at its end facing away from the head part. This extension makes the insertion of the rotary tool easier.

It is particularly advantageous when the extension is connected to the clamping screw via a predetermined breaking point which breaks when a maximum value of the screw-in torque is exceeded. As a result, the screw-in torque, with which the clamping screw can be pressed against the extension part, is limited.

It may, in addition, be provided for the head part to have a sleeve-like extension on its side facing away from the shaft. This is preferably connected to the remaining head part via a predetermined breaking point. The extension of the head part can surround the extension of the clamping screw.

In a preferred embodiment, it is provided, in addition, for the extension of the clamping screw to have on its outer side projections or recesses for a form-locking engagement of a tool. With this tool, the clamping screw can be drawn out of the head part contrary to the screw-in direction so that, as a result, prior to the secure clamping of the screw sleeve in the bearing sleeve this will be drawn into the bearing sleeve and securely clamped in it. The recess can, for example, be a circumferential groove in the wall of the extension of the clamping screw.

BRIEF DESCRIPTION OF THE DRAWINGS

The following description of preferred embodiments of the invention serves to explain the invention in greater detail in conjunction with the drawings. These show.

DETAILED DESCRIPTION

The surgical retaining screw 1 illustrated in the drawings has an elongated shaft 2 with an external thread 3 which is preferably designed as a self-cutting bone thread. The surgical retaining screw 1 can be screwed into a bone, for example, into a vertebral body 4 by means of this shaft 2.

The shaft 2 is connected to a head part 5. In the embodiments illustrated in the drawings, this connection is designed as a movable connection; it is, however, just as possible for the shaft 2 to be connected rigidly to the head part or to be pivotable only about a pivot axis extending transversely to the longitudinal direction of the shaft 2.

In the embodiments illustrated, the shaft 2 has at its upper side a spherical thickened area 6 which is arranged in the open interior space 7 of the head part 5 and which is supported at the lower end of the interior space 7 on a constriction 8 of the interior space 7 in the form of an annular shoulder. As a result, the spherical thickened area 6 is mounted in the interior space 7 so as to be pivotable to all sides and is hindered from exiting out of the interior space 7 downwardly.

The interior space 7 passes through the entire head part 5 in such a manner that the shaft 2 with the spherical thickened area 6 can be inserted into the interior space 7 from the upper side of the head part 5 until the thickened area 6 abuts on the shoulder-like constriction 8.

A clamping sleeve 9, which is pushed into the interior space 7 and abuts areally on its inner wall, is supported on the head part 5 arranged in the interior space 7, the clamping sleeve being designed at its lower edge in the shape of a spherical ring in order to correspond to the cross section of the spherical thickened area 6 and so an areal abutment on the thickened area 6 takes place. The clamping sleeve 9 has a radially projecting snap-in nose 10 which can be displaced radially inwards in an elastic manner and has an inclined slide-on surface 11 on its underside and a horizontal snap-in surface 12 on its upper side. When the clamping sleeve 9 is inserted, the snap-in nose 10 is bent elastically inwards by the snap-in surface 12 and snaps, in the pushed-in state, into a lateral opening 13 in the head part 5. When the clamping sleeve 9 is withdrawn from the interior space 7, the snap-in nose abuts on the upper edge of the opening 13 with the horizontal snap-in surface 12 and, as a result, prevents the clamping sleeve 9 from being drawn out of the interior space 7.

The head part 5 has, on two oppositely located sides, slits 14 which extend parallel to the longitudinal axis of the cylindrical interior space 7 and are open towards the upper side of the head part 5, these slits forming a receptacle for a connecting bar 15 which can be placed in the head part transversely to the central axis of the head part. In this respect, this connecting bar 15 engages in a trough-like recess 16 in the clamping sleeve 9 and abuts on it.

The side wall of the head part 5 is divided by the two slits 14 located diametrically opposite one another into two halves which are connected to one another only at the lower end of the head part 5. A bearing sleeve 19 is fixed to the upper side of these two halves 17, 18 and this sleeve accommodates a screw sleeve 20. In the embodiment illustrated in FIGS. 1 to 3, the bearing sleeve 19 has a cylindrical outer wall with a radially projecting annular shoulder 21, the upper side 22 of which rises towards the outside and upwards, i.e., towards the upper side of the head part 5; in the embodiment illustrated, the upper side 22 is of a flat design.

Figure 1:
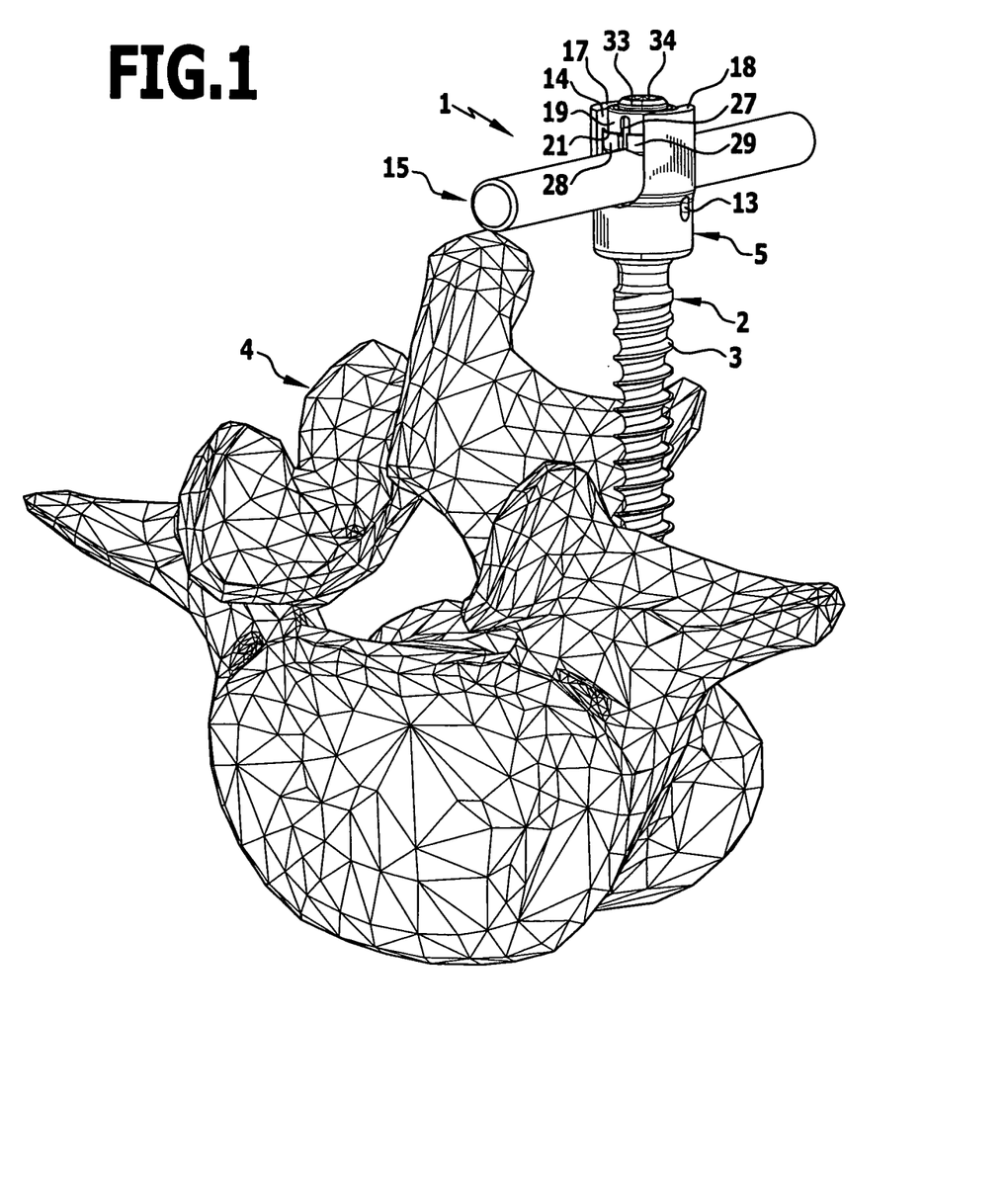
FIG. 1: a vertebral body with a surgical retaining screw screwed into it and a connecting bar held therein.
Figure 2:
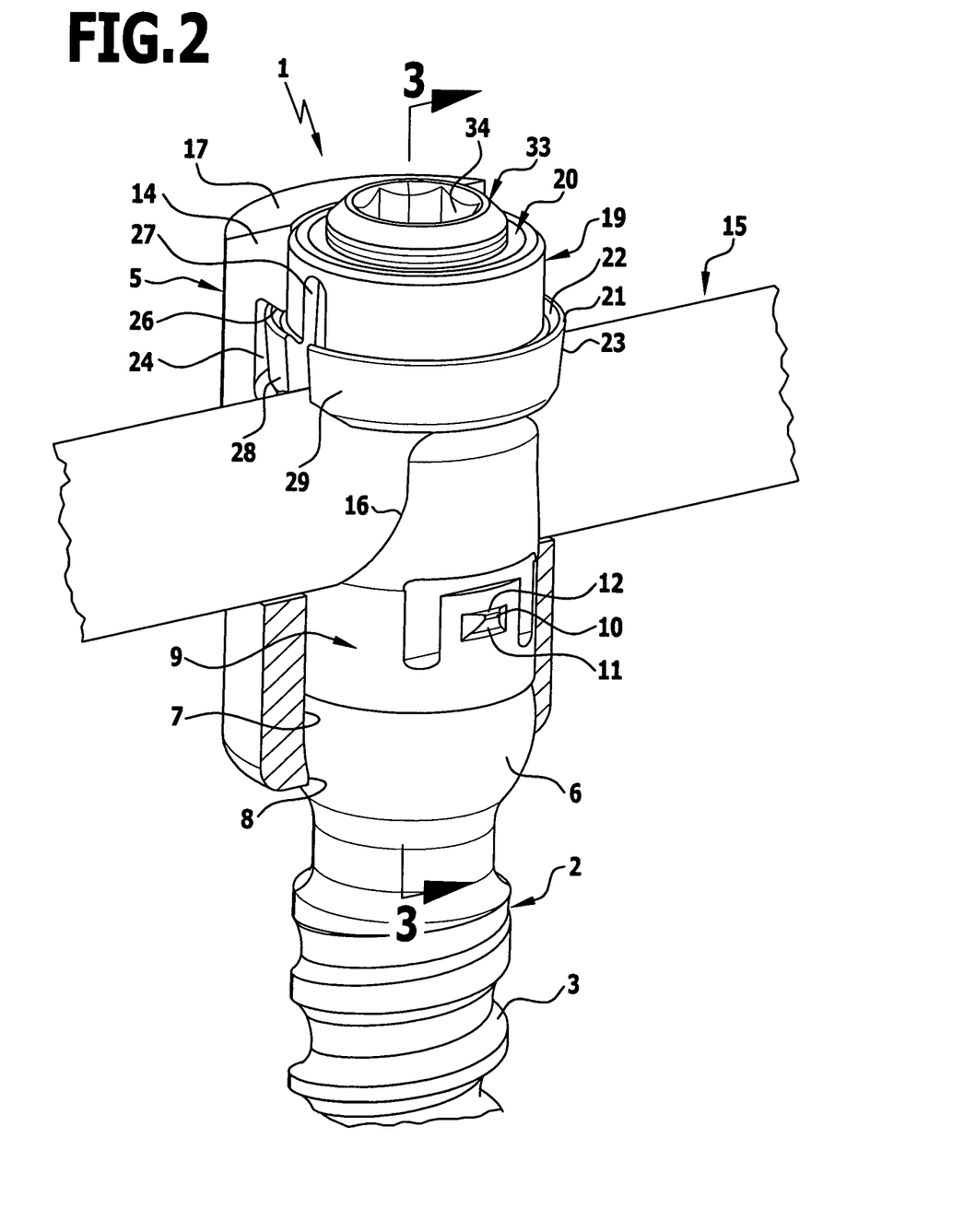
FIG. 2: an enlarged, perspective illustration of the surgical retaining screw of FIG. 1 with a head part cut in longitudinal direction.
Figure 3:
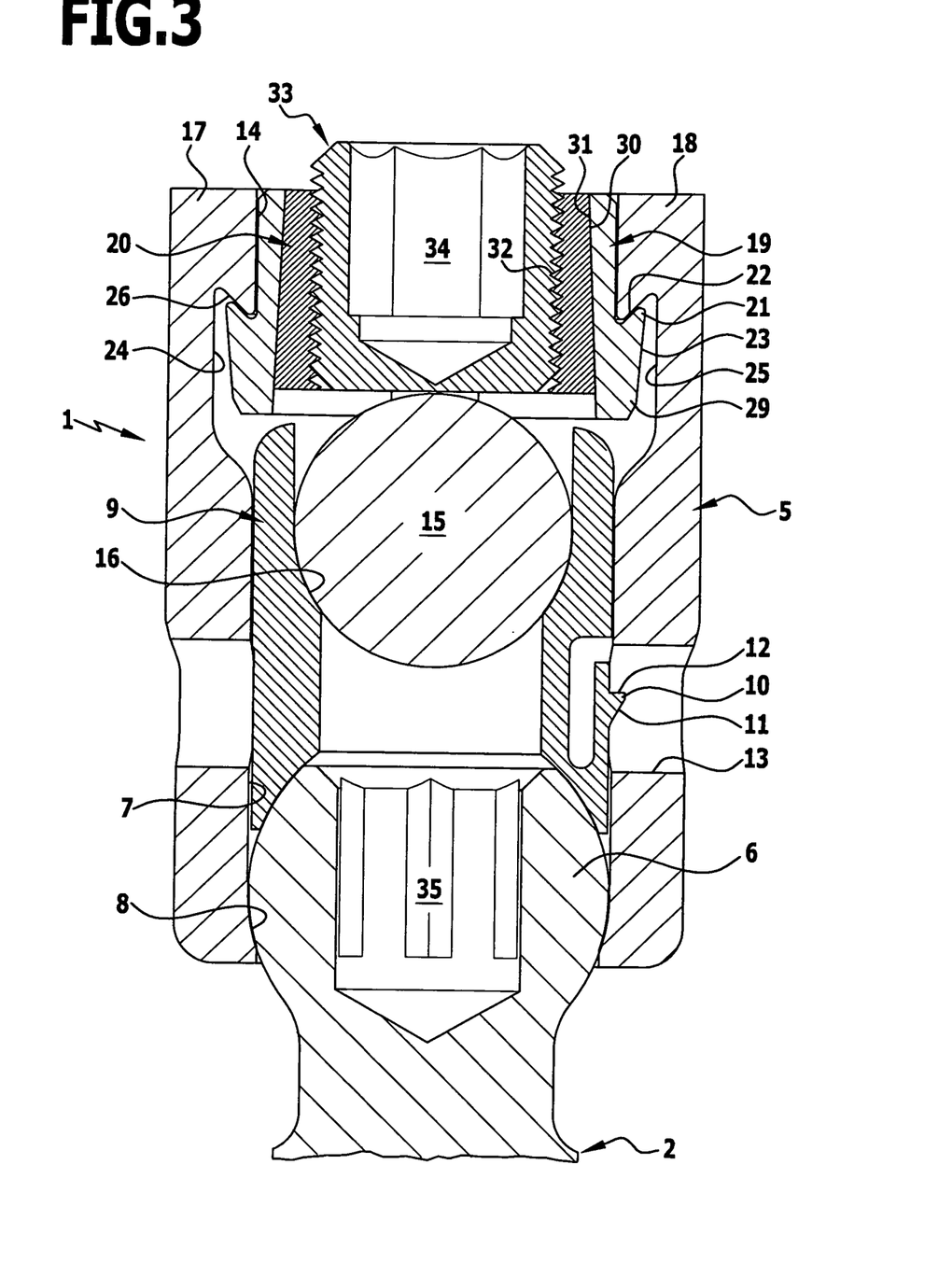
FIG. 3: a sectional view along line 3-3 in FIG. 2.

The outer surface 23 of the annular shoulder 21 which is located radially outwards has a radius which decreases from top to bottom; this side surface 23 therefore forms an inclined slide-on surface.

An arc-shaped groove 24, 25, which is open towards the interior space 7 and the upper edge 26 of which, like the upper side 22 of the annular shoulder 21, extends at an angle outwards and upwards, is let into the two halves 17, 18 of the head part 5.

The bearing sleeve 19 is divided into two halves 28, 29 by two longitudinal slits 27 which extend parallel to the central axis of the bearing sleeve, are located diametrically opposite one another and are open towards the underside of the bearing sleeve 19 and so these halves 28, 29 can be bent elastically against one another, in particular, in the area of the lower edge of the bearing sleeve 19. This deformation goes so far that the bearing sleeve 19 can be pushed into the interior space 7 from above, wherein the annular shoulder 21 abuts on the inner wall of the interior space 7 with its inclined side surface 23 acting as slide-on surface and bends the halves 28, 29 towards one another to such an extent that the annular shoulder 21 can pass the inner wall of the interior space 7 and reach as far as into the two grooves 24, 25. When the annular shoulder 21 enters the grooves 24, 25, the two halves 28, 29 can again move elastically back into the original position so that the annular shoulder 21 now enters the grooves 24, 25 completely. As a result, the bearing sleeve 19 is secured against any withdrawal since, during withdrawal out of the interior space 7, the upper side 22 of the annular shoulder 21 which extends at an angle abuts on the upper edge 26 of the grooves 24, 25 which extends at a corresponding angle and prevents any such withdrawal. In addition, the two halves 17, 18 of the head part 5 are drawn against one another during any withdrawal as a result of the inclined surfaces which abut on one another and, therefore, any spreading of the two halves 17, 18 is safely counteracted.

The outer surface 30 of the screw sleeve 20 and the inner surface 31 of the bearing sleeve 19 are both designed to be conical in the same way and taper towards the upper side of the head part 5; the conicality is slight and the cone angle is in the order of magnitude of between 0° and 30°. When the screw sleeve 20 is pushed into the bearing sleeve 19, the inner surface 31 and the outer surface 30 abut areally on one another and thus lead to a self-locking and clamping of the screw sleeve in the bearing sleeve.

The screw sleeve 20 has a continuous bore 32 with an internal thread, into which a clamping screw 33 can be screwed which has, for its part, an internal polyhedron 34 for the insertion of a rotary tool.

For the insertion of the surgical retaining screw described in FIGS. 1 to 3, the shaft with the spherical thickened area is inserted, first of all, into the head part 5; in addition, the clamping sleeve 9 is pushed in from above so that the head part 5 and the spherical thickened area 6 are connected to one another so as to be secured against loss but the thickened area 6 is freely rotatable in all directions within the head part 5.

The thickened area 6 has an internal polyhedron 35, into which a rotary tool can be introduced which can be inserted through the free interior space 7. The shaft 2 can be screwed into a bone with this rotary tool.

Following this screwing in procedure, the connecting bar 15 is placed in the head part 5 and this bar is supported on the trough-like recess 16 of the clamping sleeve 9 and is, first of all, freely displaceable and rotatable.

Subsequently, the bearing sleeve 19 with the screw sleeve 20 arranged therein is pushed into the interior space 7 from the upper side; the clamping screw 33 can already be screwed into the screw sleeve 20. However, the clamping screw is screwed in only to such an extent that the unit consisting of bearing sleeve 19, screw sleeve 20 and clamping screw 33 can be advanced into the interior space 7 deep enough for the annular shoulder 21 to be able to snap into the grooves 24, 25. Only then will the clamping screw 33 be screwed further into the screw sleeve 20 with a rotary tool, which is inserted into the internal polyhedron 34 and is not illustrated in the drawings, and abut on the upper side of the connecting bar 15 which is, as a result, pressed with increasing force against the clamping sleeve 9 the more the clamping screw is screwed in. The clamping sleeve is supported, for its part, on the spherical thickened area 6. This leads to clamping not only of the connecting bar but also of the spherical thickened area relative to the head part 5; all the movable parts are, therefore, fixed rigidly on the head part 5.

In this respect, the screw sleeve 20 is drawn forcefully into the bearing sleeve 19 so that a secure press fit is achieved. All the forces which act radially outwards and are transferred by the clamping screw 33 are absorbed by the screw sleeve 20 and, where applicable, by the bearing sleeve 19; these forces which act outwardly are not, therefore, transferred to the two halves 17, 18 of the head part 5; they are, on the contrary, drawn inwards by the inclined upper sides 22 of the annular shoulders 21.

During insertion of the surgical retaining screw 1, a rotary tool is required, first of all, only to screw in the shaft 2; during the entire assembly and alignment phase, on the other hand, no rotary tool is required until the final secure clamping by means of the clamping screw 33 is desired. It is sufficient, during assembly, for the parts to be pushed against one another; for this purpose, no tool is normally required.

Figure 8:
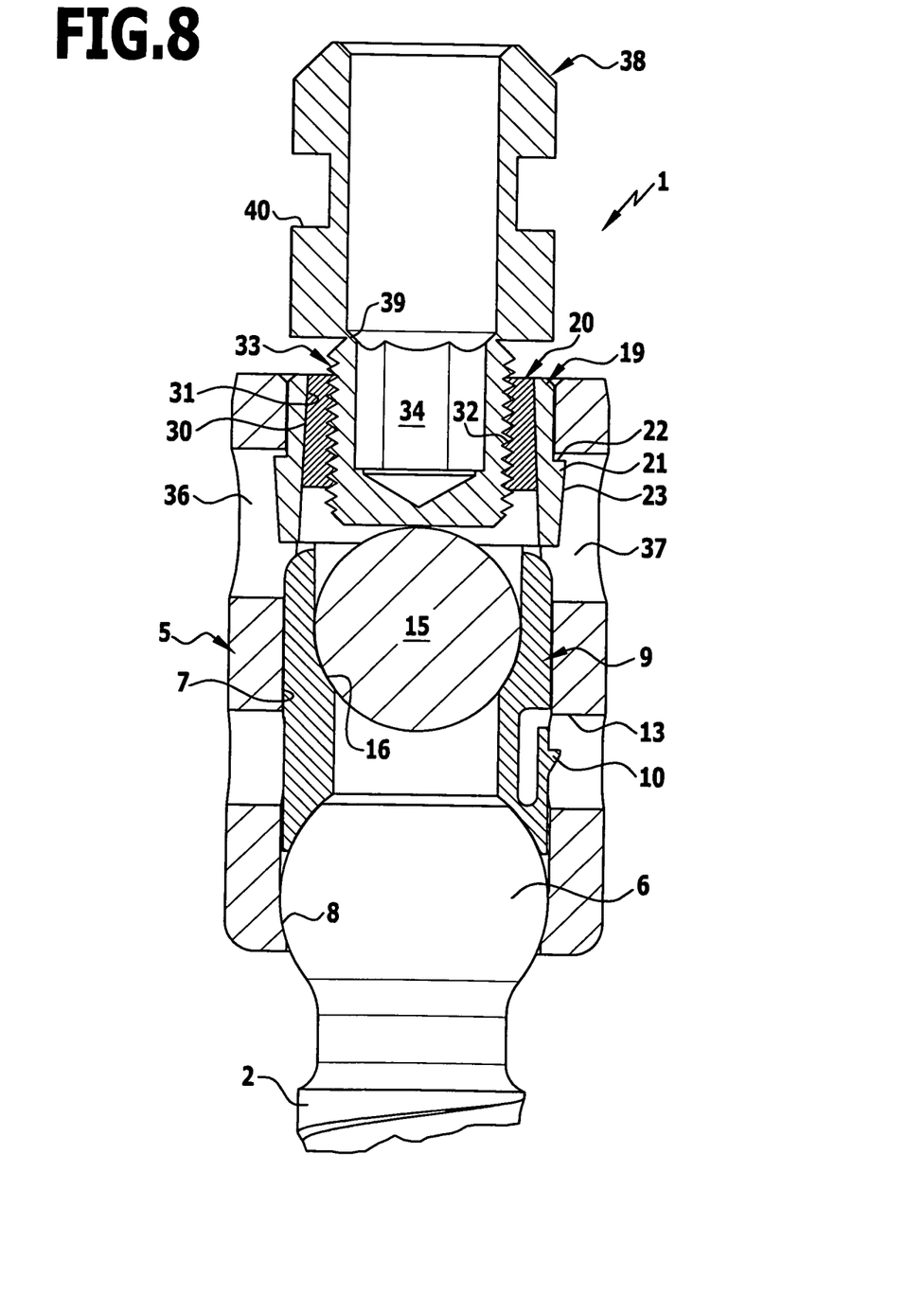
FIG. 8: a further embodiment of a surgical retaining screw in a longitudinal sectional illustration with a bearing sleeve which is secured in openings in the head part by projections.

In the embodiment illustrated in FIGS. 1 to 3, the annular shoulder 21 is supported in a groove 24, 25 of the head part 5. In the embodiment of FIG. 8, which is of a similar construction and in which corresponding parts have the same reference numerals, these grooves 24, 25 are replaced by lateral openings 36, 37 in the wall of the head part 5; in addition, it is provided in this embodiment for the upper side 22 of the annular shoulder 21 to extend horizontally and not at an angle upwards.

In the embodiment of FIG. 8, the clamping screw 33 is provided, in addition and in contrast to the embodiment of FIG. 3, with a sleeve-like extension 38 on its upper side which is connected to the upper side of the clamping screw 33 in one piece via a predetermined breaking point 39 and which has a circumferential groove 40 in its outer side.

This circumferential groove serves to accommodate a tool which is not shown in the drawings and which can subject the clamping screw 33 with its extension 38 to a pulling force which extends from bottom to top and, therefore, leads to the clamping screw with the screw sleeve 20, into which the clamping screw is screwed, being drawn further into the bearing sleeve 19. With such a tool, a clamping connection can be provided between the screw sleeve and the bearing sleeve once the constructional unit consisting of bearing sleeve, screw sleeve and clamping screw has been inserted. The pulling force can be limited by the predetermined breaking point 39 which gives way when a specific pulling force is exceeded.

It may also be provided for the extension 38 to form a form-locking connection with a rotary tool, for example, by means of an internal polyhedron and so the screw-in forces for the clamping screw are transferred via the extension 38. In this way, the predetermined breaking point 39 can serve the purpose of limiting the screw-in torque.

Figure 4:
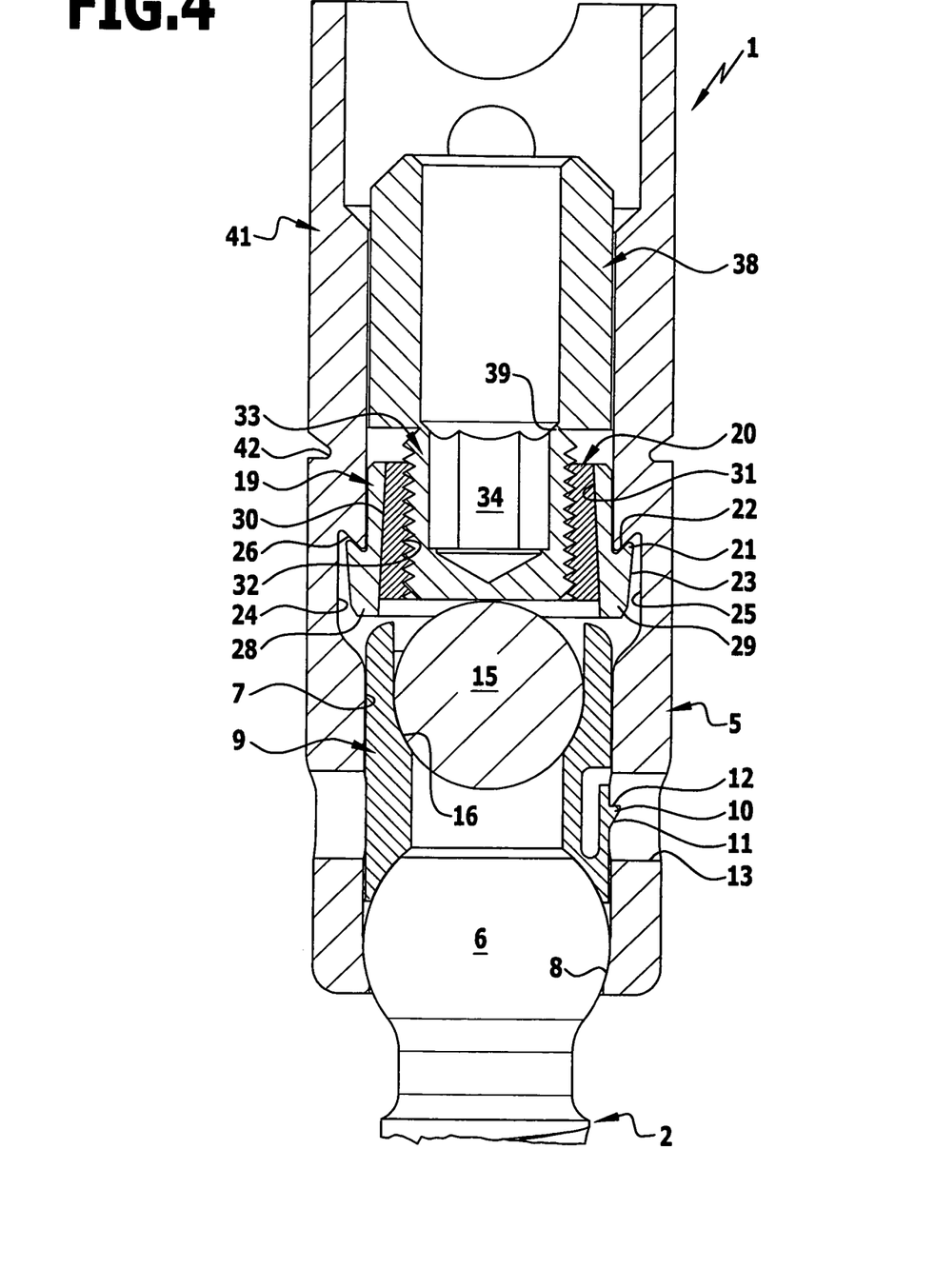
FIG. 4: a view similar to FIG. 3 in a modified embodiment of a surgical retaining screw with a clamping screw with an extension and a head part with an extension.

In the embodiment of FIG. 4, a configuration is selected which is similar to that of the embodiment of FIG. 3; in this case, as well, the clamping screw 33 has an extension, in this case, however, without any circumferential groove in the outer wall. This extension 38 of the clamping screw 33 is, in this embodiment, surrounded by a sleeve-like extension 41 of the head part 5. This extension 41 is also connected to the head part 5 via a predetermined breaking point 42 and can, therefore, be separated when certain forces are exceeded.

Figure 5:
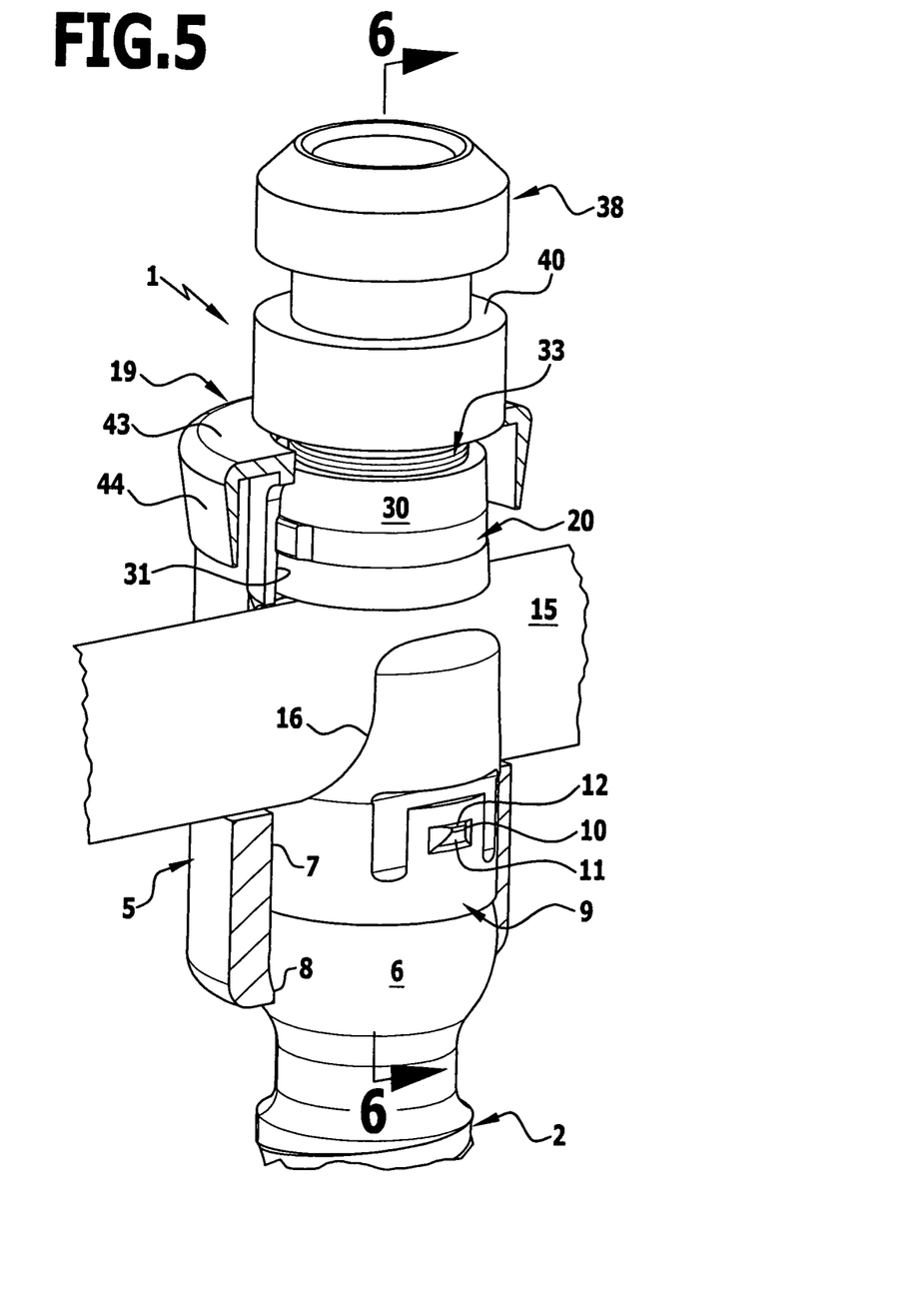
FIG. 5: a view similar to FIG. 2 in a modified embodiment with a clamping screw with an extension and a bearing sleeve engaging around the head part on the upper side.
Figure 6:
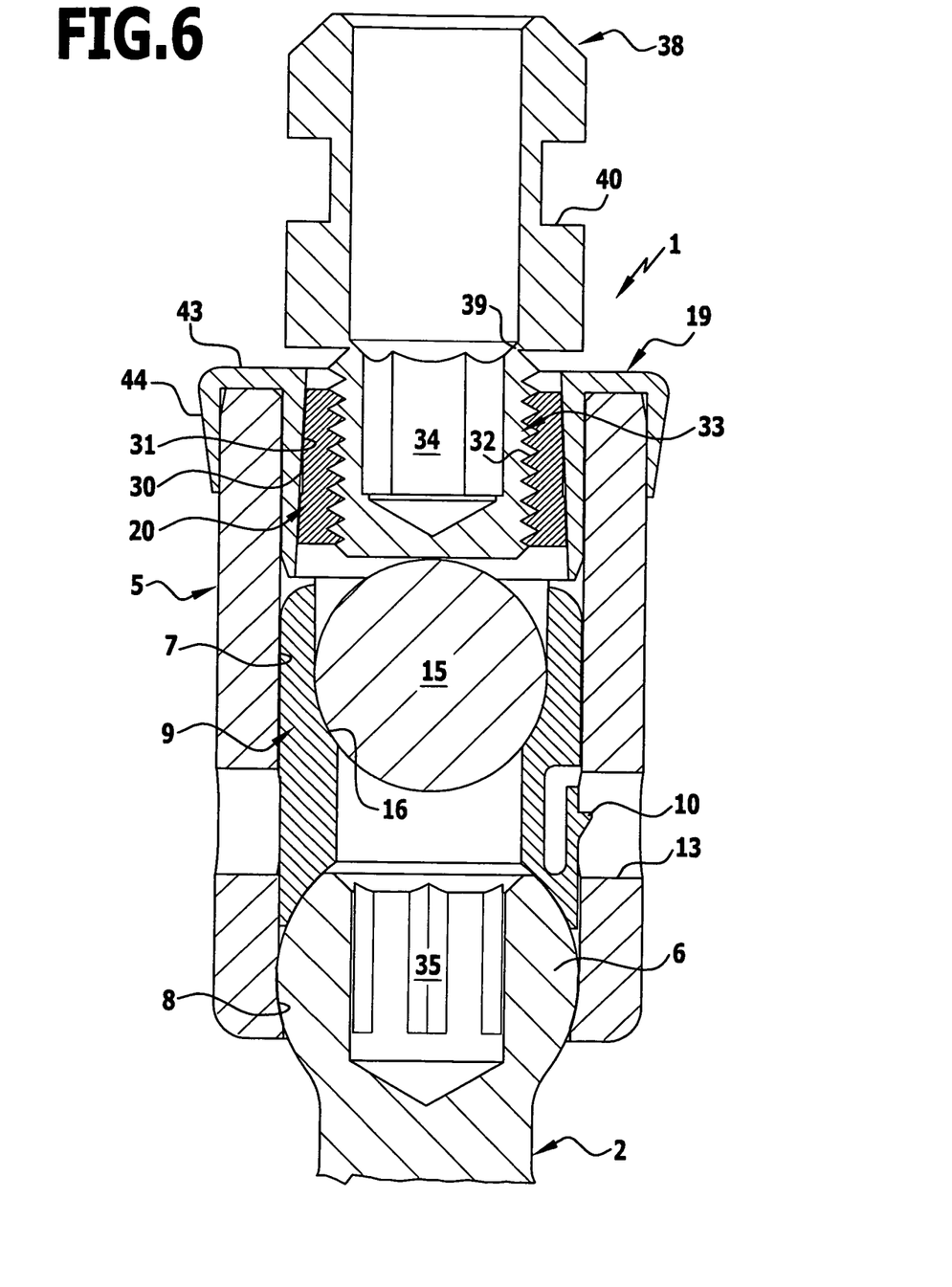
FIG. 6: a sectional view along line 6-6 in FIG. 5.
Figure 7:
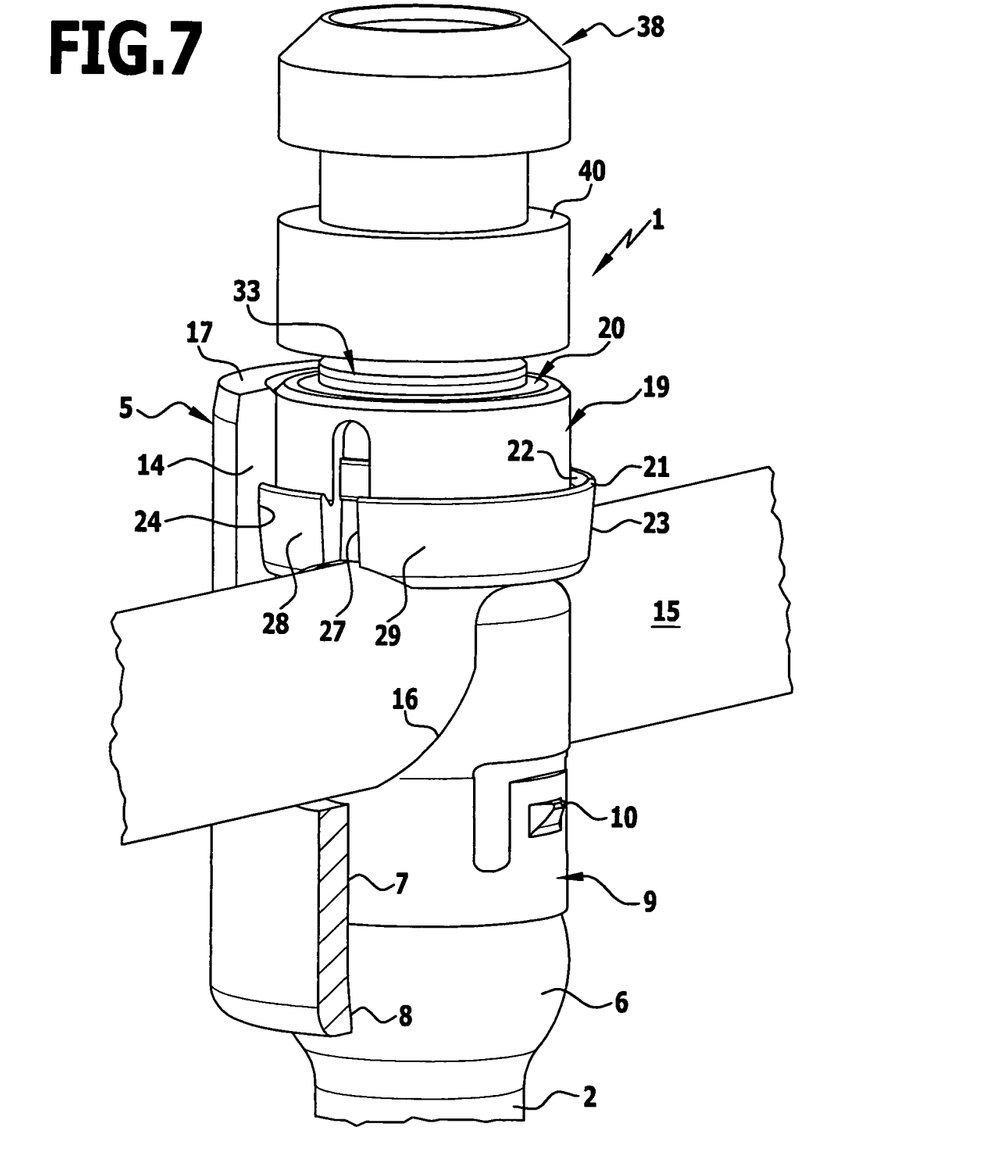
FIG. 7: a view similar to FIG. 5 with a bearing sleeve completely inserted into the head part.

In the embodiment of FIGS. 5 and 6, a construction is selected which is similar to that of the embodiments of FIGS. 7 and 8. Parts which correspond to one another therefore have the same reference numerals. In contrast to the embodiments of FIGS. 7 and 8, the bearing sleeve 19 is not supported on the head part 5, in this embodiment, via an annular shoulder engaging in a groove or an opening but rather the bearing sleeve 19 engages with a cylindrical outer wall in the interior space 7 of the head part 5 and is pressed radially against the inner wall of the interior space 7 in this area by the expanding cone effect of the screw sleeve 20 such that a frictional connection results. This frictional connection leads to the bearing sleeve 19 likewise being secured against any movement upwards.

In this embodiment, the bearing sleeve 19 abuts on the upper side and the outer side of the head part 5 with a flange 43 which projects radially from the upper edge and a cylindrical edge strip 44 which adjoins the outer edge of this flange 43; the edge strip 44, the flange 43 and the cylindrical wall of the bearing sleeve 19 therefore form a channel, in which the upper edge of the head part 5 engages.

Figure 9:
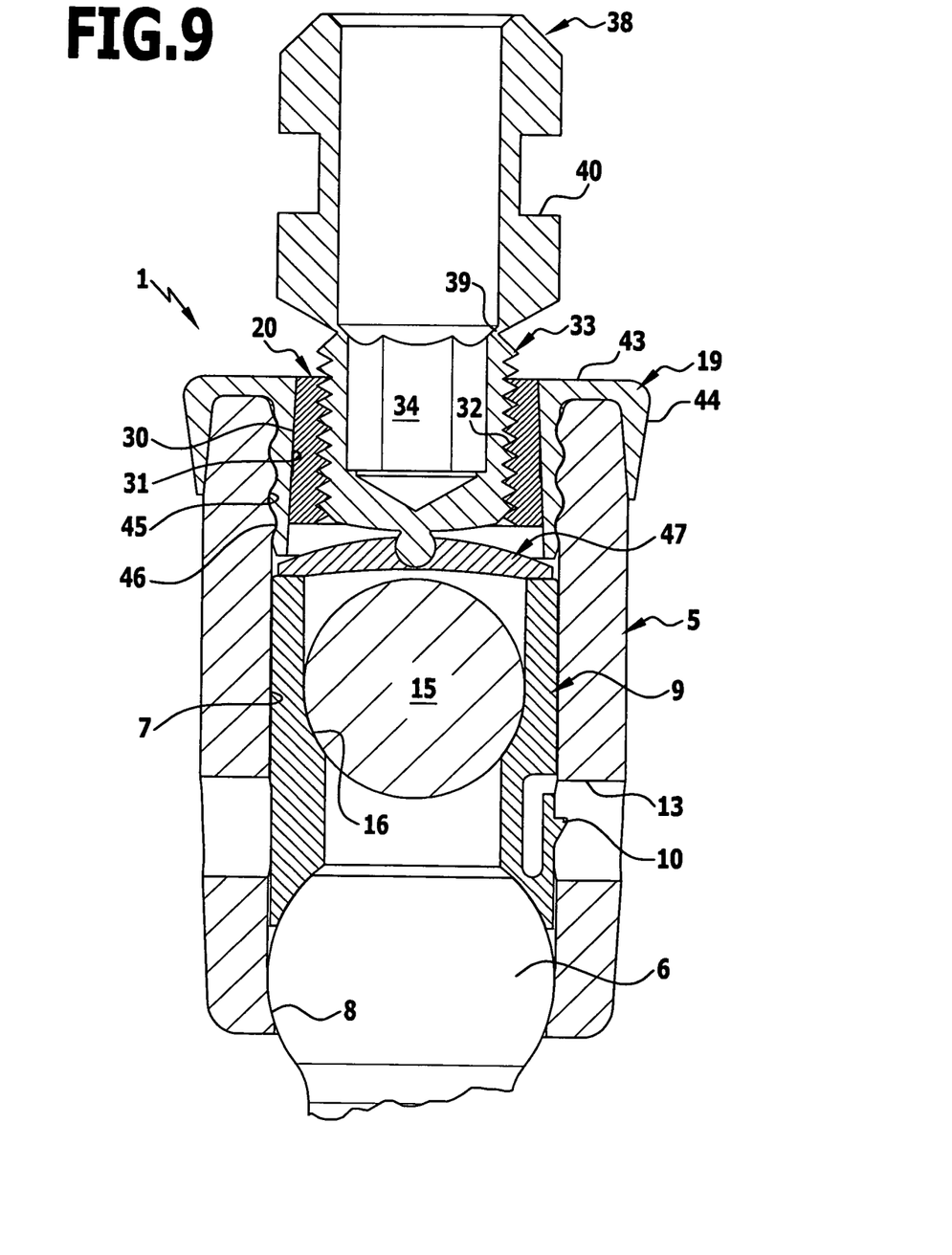
FIG. 9: a view of an additional, preferred embodiment of a surgical retaining screw similar to that of FIG. 6 with a clamping screw which fixes the connecting part in the head part via an elastic clamping element.

A similar configuration is illustrated in the embodiment of FIG. 9, with which parts which correspond to one another likewise have the same reference numerals. To improve the secure positioning of the bearing sleeve 19, a form-locking connection is also provided in this case in addition to the frictional connection; for this purpose, not only the cylindrical outer surface of the bearing sleeve 19 but also the inner wall of the head part 5 have circumferential channels 45, 46 which engage in one another in a form-locking manner. These channels 45, 46 are designed such that it is possible to push the bearing sleeve 19 in owing to elastic deformation of the bearing sleeve 19 and/or of the head part 5 but that a form-locking engagement and, therefore, a secure fixing in position of the bearing sleeve 19 on the head part 5 are brought about with the spreading effect of the screw sleeve 20 drawn into the bearing sleeve 19.

Whereas, in the embodiments of FIGS. 1 to 8, the clamping screw 33 is supported directly on the connecting bar 15, it is provided in the embodiment of FIG. 9 for the clamping screw 33 to abut on a resilient clamping element 47 which is supported, for its part, on the upper edge of the clamping sleeve 9. When the clamping screw 33 is screwed in, the clamping sleeve 9 is, as a result, pressed first of all against the spherical thickened area 6, i.e., the shaft 2 is fixed in position in relation to the head part 5 whereas the connecting bar is still freely movable. Only when the clamping screw 33 is screwed in further will the clamping element 47 be bent elastically downwards and abut on the upper side of the connecting bar 15 which is then, likewise, securely clamped, namely as a result of secure clamping in the recess 16 of the clamping sleeve 9. As a result, a two-step fixing in position of the movable parts can take place when the clamping screw is screwed in, first of all fixing the shaft 2 with the spherical thickened area 6 in position and only then fixing the connecting bar 15 in position.

What is claimed is:

1. Surgical retaining screw, comprising:
   a shaft with an external thread,
   a head part connected to the shaft securely or movably, said head part having an interior space open towards an upper side of the head part located opposite the shaft and two openings arranged on oppositely located sides of the head part, said openings being open towards the upper side and forming a receptacle for a bar-like connecting part, and
   a clamping screw adapted to be screwed into the interior space from the upper side such that it clamps the connecting part in the receptacle,
   wherein:
   the clamping screw is screwed into a monolithic screw sleeve,
   the screw sleeve abuts, with a conical outer surface tapering towards the upper side of the head part, directly on a complementary conical inner surface of a bearing sleeve surrounding the screw sleeve,
   the screw sleeve and the bearing sleeve are adapted to cooperate together to absorb forces from the clamping screw acting radially outward in order to prevent a spreading apart of the head part during screwing in of the clamping screw,
   the bearing sleeve and the clamping screw are not screwed together, and
   the bearing sleeve is held on the head part so as to be secured against any displacement in a direction towards the upper side.

2. Surgical retaining screw as defined in claim 1, wherein an angle of inclination of the conical outer surface in relation to a central axis of the screw sleeve is between 0° and 30°.

3. Surgical retaining screw as defined in claim 1, wherein:
   the bearing sleeve is arranged in the interior space, and
   in order to secure the bearing sleeve against any displacement in the direction towards the upper side of the head part, the bearing sleeve and the head part have one or more projections and recesses engaging in one another.

4. Surgical retaining screw as defined in claim 3, wherein the bearing sleeve has, on an outer side, one or more projections engaging in recesses on an inner side of the head part.

5. Surgical retaining screw as defined in claim 3, wherein each of the one or more projections on the bearing sleeve is an annular shoulder projecting outwardly.

6. Surgical retaining screw as defined in claim 5, wherein each of the one or more recesses is an arc-shaped groove on an inner side of the interior space.

7. Surgical retaining screw as defined in claim 5, wherein the annular shoulder has an upper side ascending towards an outside of the interior space.

8. Surgical retaining screw as defined in claim 7, wherein each of the one or more recesses has an upper side sloping down towards the interior space.

9. Surgical retaining screw as defined in claim 3, wherein each of the one or more recesses is formed by an opening in a wall of the head part.

10. Surgical retaining screw as defined in claim 3, wherein the bearing sleeve and the head part are designed such that the bearing sleeve is adapted to be pushed into the interior space from the upper side of the head part until the one or more projections engage in the one or more recesses of the head part.

11. Surgical retaining screw as defined in claim 10, wherein the bearing sleeve is adapted to be compressed radially in an area of the one or more projections or recesses.

12. Surgical retaining screw as defined in claim 11, wherein the bearing sleeve is subdivided by longitudinal slits into sections located next to one another and adapted to be bent elastically against one another.

13. Surgical retaining screw as defined in claim 10, wherein the head part is adapted to be expanded elastically in an area of the one or more projections or recesses.

14. Surgical retaining screw as defined in claim 10, wherein the one or more projections have slide-on surfaces making entry of the one or more projections into the one or more recesses possible during the insertion of the bearing sleeve into the interior space.

15. Surgical retaining screw as defined in claim 10, wherein the one or more projections and recesses are circumferential grooves on an outer side of the bearing sleeve and an inner side of the head part.

16. Surgical retaining screw as defined in claim 1, wherein the bearing sleeve has a radially projecting flange abutting on the upper side of the head part when the bearing sleeve is inserted.

17. Surgical retaining screw as defined in claim 16, wherein the radially projecting flange has, at an outer edge, an annular wall section abutting on an outer wall of the head part when the bearing sleeve is inserted.

18. Surgical retaining screw as defined in claim 1, wherein the clamping screw abuts directly on the connecting part in a screwed-in state.

19. Surgical retaining screw as defined in claim 1, wherein the clamping screw abuts in a screwed-in state on a clamping element pressed onto the connecting part by the clamping screw when screwed in.

20. Surgical retaining screw as defined in claim 1, wherein the clamping screw has an extension for accommodating a rotary tool at an end facing away from the head part.

21. Surgical retaining screw as defined in claim 20, wherein the extension is connected to the clamping screw via a predetermined breaking point breaking when a maximum value of a screw-in torque is exceeded.

22. Surgical retaining screw as defined in claim 20, wherein the extension of the clamping screw has on an outer side projections or recesses for a form-locking engagement of a tool.

23. Surgical retaining screw as defined in claim 1, wherein the head part has a sleeve-like extension on a side facing away from the shaft.

24. Surgical retaining screw as defined in claim 23, wherein the extension is connected to the head part via a predetermined breaking point.

25. Surgical retaining screw as defined in claim 24, wherein the extension of the head part surrounds an extension of the clamping screw.

\* \* \* \* \*